(12) United States Patent
Veirman et al.

(10) Patent No.: US 10,371,657 B2
(45) Date of Patent: Aug. 6, 2019

(54) METHOD FOR LOCATING A WAFER IN THE INGOT OF SAME

(71) Applicant: COMMISSARIAT À L'ENERGIE ATOMIQUE ET AUX ENERGIES ALTERNATIVES, Paris (FR)

(72) Inventors: Jordi Veirman, Poisy (FR); Sébastien Dubois, Scionzier (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 655 days.

(21) Appl. No.: 14/909,230

(22) PCT Filed: Aug. 1, 2014

(86) PCT No.: PCT/FR2014/000179
§ 371 (c)(1),
(2) Date: Feb. 1, 2016

(87) PCT Pub. No.: WO2015/015065
PCT Pub. Date: Feb. 5, 2015

(65) Prior Publication Data
US 2016/0187278 A1 Jun. 30, 2016

(30) Foreign Application Priority Data

Aug. 2, 2013 (FR) ................................ 13 01875

(51) Int. Cl.
*G01R 27/08* (2006.01)
*G01N 27/04* (2006.01)
(Continued)

(52) U.S. Cl.
CPC ....... *G01N 27/041* (2013.01); *G01N 21/3504* (2013.01); *G01N 21/9501* (2013.01);
(Continued)

(58) Field of Classification Search
CPC .......... G01N 21/9501; G01N 21/3504; G01N 27/041; G01N 27/125; G01N 2033/0095;
(Continued)

(56) References Cited

U.S. PATENT DOCUMENTS 6,482,661 B1 11/2002 Madoyski
2003/0196586 A1* 10/2003 Falster ................ H01L 21/3225
117/2

(Continued)

FOREIGN PATENT DOCUMENTS

FR 2964459 A1 3/2012
JP 2001-076981 A 3/2001

OTHER PUBLICATIONS

Nov. 28, 2014 Search Report issued in International Patent Application No. PCT/FR2014/000179.
(Continued)

*Primary Examiner* — Thang X Le
(74) *Attorney, Agent, or Firm* — Oliff PLC

(57) ABSTRACT

A method for determining the original position of a wafer in an ingot made from semiconductor material comprises the following steps: measuring the interstitial oxygen concentration in an area of the wafer; measuring the concentration of thermal donors formed in said area of the wafer during a previous solidification of the ingot; determining the effective time of a thermal donor formation anneal undergone by the wafer when solidification of the ingot took place, from the thermal donor concentration and the interstitial oxygen concentration; and determining the original position of the wafer in the ingot from the effective time.

9 Claims, 4 Drawing Sheets

(51) Int. Cl.
    *G01N 21/95*     (2006.01)
    *H01L 21/66*     (2006.01)
    *G01N 21/3504*     (2014.01)
    *G01R 31/26*     (2014.01)
    *G01N 33/00*     (2006.01)

(52) U.S. Cl.
    CPC .......... *G01R 31/2601* (2013.01); *H01L 22/12*
    (2013.01); *H01L 22/14* (2013.01); *H01L 22/20*
    (2013.01); *G01N 2033/0095* (2013.01)

(58) Field of Classification Search
    CPC ....... G01N 25/005; H01L 22/12; H01L 22/14;
        H01L 22/20; H01L 31/0747; H01L
        31/208; H01L 31/202; H01L 31/068;
        H01L 31/1804; H01L 31/03529; G01R
        31/2601; G06F 17/11
    See application file for complete search history.

(56) References Cited

U.S. PATENT DOCUMENTS

| | | | | |
|---|---|---|---|---|
| 2006/0213424 | A1* | 9/2006 | Mueller | .................. C30B 25/12 |
| | | | | 117/15 |
| 2006/0282229 | A1* | 12/2006 | Kim | ........................ C30B 15/26 |
| | | | | 702/83 |
| 2010/0224968 | A1* | 9/2010 | Kurita | ..................... C30B 15/00 |
| | | | | 257/655 |
| 2013/0158889 | A1 | 6/2013 | Veirman et al. | |
| 2014/0291809 | A1* | 10/2014 | Schulze | .................. H01L 21/22 |
| | | | | 257/607 |
| 2015/0371858 | A1* | 12/2015 | Laven | ............... H01L 29/66712 |
| | | | | 438/530 |

OTHER PUBLICATIONS

Corbett, J.W. et al. "New Oxygen Infrared Bands in Annealed Irradiated Silicon". Physical Review, vol. 135, No. 5A, Aug. 31, 1964, pp. A1381-A1385, XP055114040.

Morin, L.I. et al. "Experimental Evidence of the Oxygen Dimer in Silicon". Physical Review Letters, vol. 80, No. 1, Jan. 5, 1998, pp. 93-96, XP055114044.

Wijaranakula, W. et al. "Formation Kinetics of Oxygen Thermal Donors in Silicon". Applied Physics Letters, vol. 59, No. 13, Sep. 23, 1991, pp. 1608-1610, XP055114038.

Wada, Kazumi. "Unified Model for Formation Kinetics of Oxygen Thermal Donors in Silicon". Physical Review, B. Condensed Matter, American Institute of Physics. New York, US, vol. 30, No. 10, Nov. 15, 1984, pp. 5884-5895, XP002696153.

Londos, C.A. et al. "Effect of Oxygen Concentration on the Kinetics of Thermal Donor Formation in Silicon At Temperatures Between 350 and 500° C.". Applied Physics Letters, vol. 62, No. 13, Mar. 29, 1993, pp. 1525-1526.

* cited by examiner

METHOD FOR LOCATING A WAFER IN THE INGOT OF SAME

BACKGROUND OF THE INVENTION

The invention relates to characterization techniques of semiconductor wafers, and more particularly to a method for determining the original position of the wafers in the ingot from which they originate.

STATE OF THE ART

After a semiconductor ingot has been crystallised, it is diced into a plurality of wafers or substrates. These wafers are then sold in batches to be used in fabrication of integrated circuits or of solar cells.

The manufacturers of such components set up identification solutions for monitoring the wafers throughout the fabrication process. These solutions, along with a suitable management software tool, enable them to record information concerning the wafer or the corresponding batch, for example the historical account of the fabrication steps.

In general, integrated circuit or solar cell manufacturers do not have any knowledge of the original position of the wafers in their ingot. This information is not communicated by the ingot manufacturer, essentially for economic and traceability reasons. However, this information is crucial for the wafer user, as the defects and impurities are not uniformly distributed in a semiconductor ingot. For example, the top part of the ingot, solidified first when the ingot is pulled, contains a large quantity of oxygen. The bottom part of the ingot, which is solidified last, is rich in metallic impurities. This results in the electric and mechanical properties of the wafers varying considerably from one portion of the ingot to another.

At the present time, the initial position of the wafers in the ingot cannot be determined without indications from the ingot manufacturer. Even when such information is available, the latter may be partial or even erroneous.

SUMMARY OF THE INVENTION

A requirement therefore exists to provide a method for subsequent determination of the original position of a wafer in an ingot made from semiconductor material.

According to the invention, this requirement tends to be satisfied by providing the following steps:
  measuring the interstitial oxygen concentration in one area of the wafer;
  measuring the concentration of thermal donors formed in said area of the wafer during a previous solidification of the ingot;
  determining the effective time of a thermal donor formation anneal undergone by the wafer when solidification of the ingot took place from the thermal donor concentration and the interstitial oxygen concentration; and
  determining the original position of the wafer in the ingot from the effective time.

According to a development of the invention, the thermal donor concentration is determined from two resistivity values measured in said area of the wafer before and after heat treatment performed for the purposes of destroying the thermal donors.

According to another development, which is compatible with the previous development, the interstitial oxygen concentration is determined from two resistivity values measured in said area of the wafer before and after an additional thermal donor formation anneal.

In a preferred embodiment of the invention, the thermal donor destruction heat treatment is performed after the additional thermal donor formation anneal.

The original position of the wafer can be determined by means of an abacus, established according to the following steps:
  selecting a plurality of wafers originating from the same ingot;
  determining a value of the effective time for each wafer;
  placing two points corresponding to the minimum and maximum values of the effective time from the set of previously determined effective time values on the abacus; and
  plotting a straight line between the two points.

The minimum and maximum effective time values are preferably associated with original positions equal to 5% and 85% of the total height of the ingot.

BRIEF DESCRIPTION OF THE DRAWINGS

Other advantages and features will become more clearly apparent from the following description of particular embodiments given for non-restrictive example purposes only and illustrated by means of the appended drawings, in which.

DESCRIPTION OF A PREFERRED EMBODIMENT OF THE INVENTION

Silicon ingots obtained by conventional crystallisation techniques, for example by the Czochralski process for monocrystalline silicon and the Bridgman process for polycrystalline silicon, contain oxygen. The oxygen atoms in particular occupy interstitial positions in the crystal lattice(s).

During crystallisation of silicon, the temperature of the ingot decreases slowly, going from 1414° C. (melting temperature of silicon) down to ambient temperature (about 25° C.). However between 350° C. and 500° C., the oxygen in interstitial position forms clusters called thermal donors (TD). The thermal donors have the particularity of generating free electrons. They therefore have a doping nature and influence the electric properties of the silicon.

Thermal donors therefore exist in an ingot on completion of solidification of the latter, and they consequently exist in the wafers which originate from this ingot. The thermal donor concentration is however not uniform over the height of the ingot. This is due to the fact that the different portions of the ingot are not cooled at the same rate and that they do not contain the same interstitial oxygen content.

Figure 1:
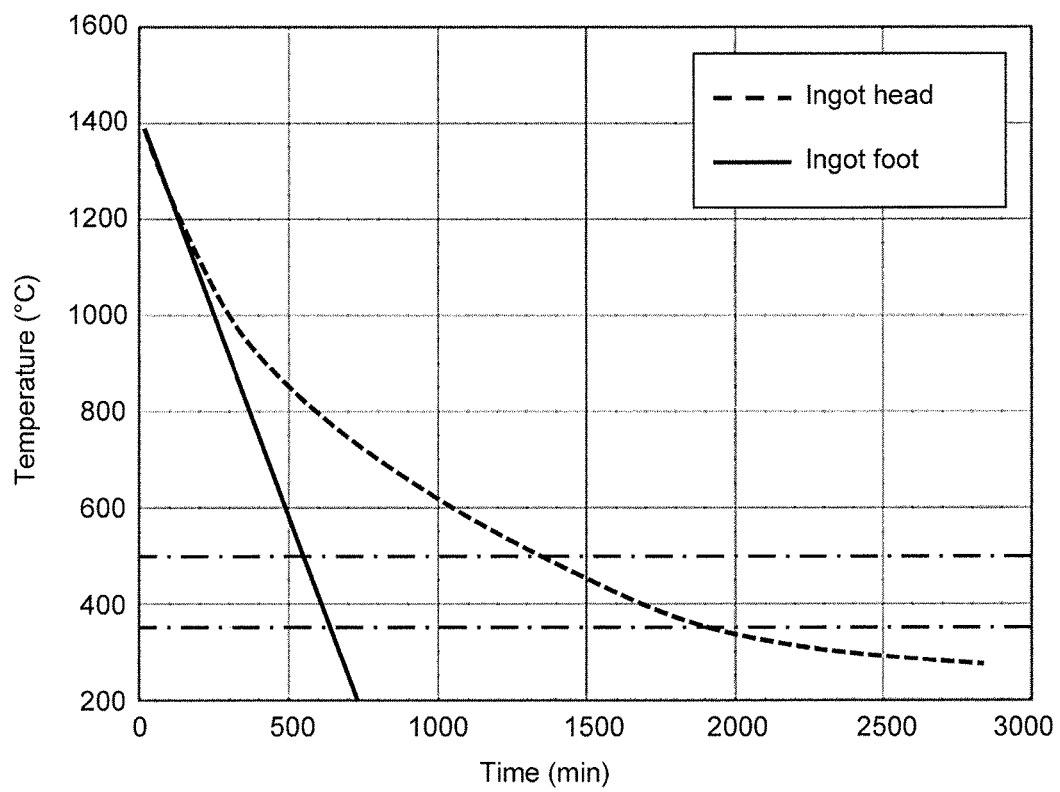
FIG. 1 represents the variation of the temperature of a portion at the head of the ingot and of a portion at the foot of the ingot, when solidification of the latter takes place.

FIG. 1 represents the temperature profiles of the top and bottom ends of a silicon ingot when pulling is performed by means of the Czochralski method. The temperature curve of the top end, called head of the ingot, is represented by a dashed line, whereas the temperature curve of the bottom end, called foot of the ingot, is represented by a straight line.

As illustrated by FIG. 1, the temperature at the head of the ingot decreases more slowly than the temperature at the foot of the ingot with time. Indeed, after solidification of the top part of the ingot, the latter remains in heat exchange with the molten silicon bath throughout the duration of the pulling, via the body of the ingot in formation. At the end of pulling on the other hand, the bottom portion solidifies and the ingot is then removed from the bath, which explains why the temperature of the foot of the ingot decreases more rapidly.

On account of these different cooling kinetics, the head of the ingot spends more time than the foot of the ingot in the temperature range corresponding to the formation of thermal donors. In the example of an ingot of FIG. 1, the head of the ingot spends more than 600 minutes in the 350° C.-500° C. range (represented by a dot-dashed line), whereas the foot of the ingot only remains in this range for 80 minutes.

The intermediate portions of the silicon ingot, i.e. those situated between the head and the foot, see their temperature decrease at a rate comprised between the two curves. Consequently, the time during which these portions have a temperature comprised in the 350° C.-500° C. range is situated between 80 min and 600 min.

The effective formation time $t_{eff}$ of thermal donors during solidification of a portion of the ingot therefore depends on the position h of this portion in the ingot. It is further observed that the function $t_{eff}(h)$ is strictly increasing or decreasing depending on whether the foot or the head is considered as being the origin of the positions in the ingot. In other words, a bijection relation exists between the time $t_{eff}$ and the position h in the ingot: there is a single time $t_{eff}$ corresponding to each portion of the ingot.

This observation is put into application in the following to determine the origin of a silicon wafer in the ingot. The effective formation time $t_{eff}$ of the thermal donors (between 350° C. and 500° C.) is determined from readings of the interstitial oxygen concentration and of the thermal donor concentration initially present in the wafer.

Figure 2:
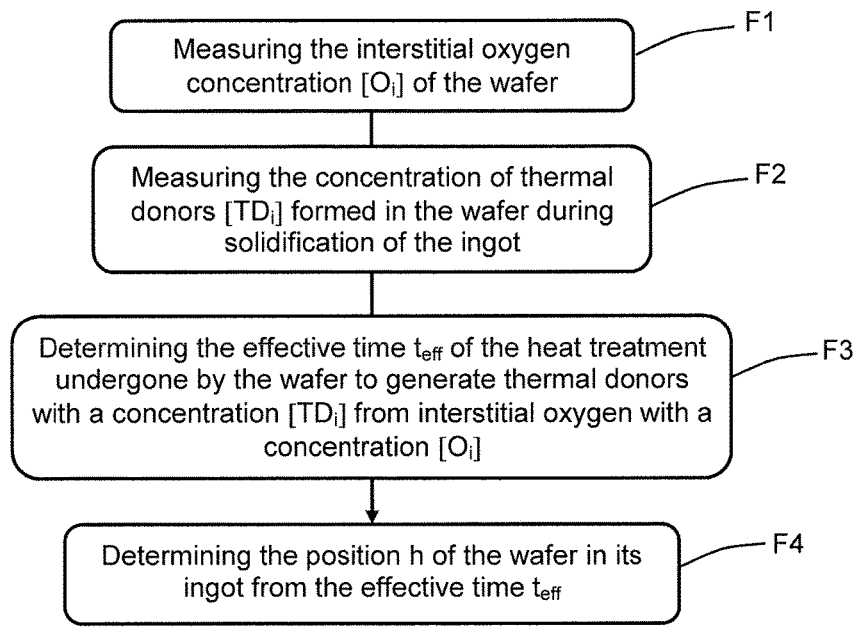
FIG. 2 represents steps of a method for determining the original position of a semiconductor wafer in its parent ingot.

FIG. 2 represents steps F1 to F4 of this silicon wafer location method.

In F1, the interstitial oxygen concentration, noted $[O_i]$, is determined in at least one area of the wafer. The concentration $[O_i]$ can in particular be measured by secondary ion mass spectrometry (SIMS) or by Fourier transform infrared spectroscopy (FTIR). The latter technique enables the absorption of an infrared radiation in semiconductor material versus the wavelength of this radiation to be measured. As the interstitial oxygen contributes to this absorption, it is possible to deduce the concentration $[O_i]$ from the absorption measurement.

Step F2 consists in determining the initial thermal donor concentration $[TD]_i$ in the same area or areas of the wafer. As indicated in the foregoing, these thermal donors appeared during cooling of the ingot, between 350° C. and 500° C.

Again, the FTIR technique can be used for measuring the concentration $[TD]_i$, as the thermal donors also have an influence on absorption of the infrared radiation. Like oxygen, the thermal donors make characteristic peaks appear in the absorption spectrum. A family of thermal donors corresponds to each peak (a total of 16 families identified, all having the same donor behaviour). The thermal donor concentration $[TD]_i$ is calculated by converting the amplitude of the absorption peaks and by adding the values obtained.

Thus, on completion of step F2, one or more pairs of the values $[O_i]$ and $[TD]_i$ have been defined.

In step F3, the effective time $t_{eff}$ of the heat treatment between 350° C. and 500° C. that enabled formation of the thermal donors with the concentration $[TD]_i$ is determined from the oxygen content $[O_i]$.

The effective time $t_{eff}$ is preferably calculated from the values of $[O_i]$ and $[TD]_i$ measured in steps F1 and F2 by means of a relation taken from the article ["Formation kinetics of oxygen thermal donors in silicon", Wijaranakula C. A. et al., Appl. Phys. Lett. 59 (13), pp. 1608, 1991]. This article describes the formation kinetics of the thermal donors in silicon by an anneal at 450° C.

The time $t_{eff}$ is then considered to be equivalent to the duration of an anneal at 450° C. which would have had to be used to obtain a thermal donor concentration equal to $[TD]_i$, from an oxygen concentration equal to $[O_i]$.

According to the above-mentioned article, the concentration $[TD]_i$, the concentration $[O_i]$ and time t of the anneal at 450° C. are linked by the following relation:

$$[TD]_i = 4.51 * 10^{-52} \times \left([O_i]\left(1 + \frac{2}{3}D_o \times t \times [O_i]^{2/3}\right)^{-3/2}\right)^{3.45} \times t^{1.02} \quad (1)$$

with $D_o$ the diffusion coefficient of the interstitial oxygen at 450° C. ($D_o=3.5*10^{-19}$ cm²/s).

The equivalent time t thus calculated constitutes a good approximation of the effective time $t_{eff}$, i.e. the time the wafer spent in the 350° C.-500° C. temperature range when solidification of the ingot took place.

To calculate the time $t_{eff}$, relation (1) above is privileged as the temperature of 450° C. is that at which the thermal donor formation kinetics are best documented. Annealing at 450° C. has been the subject of numerous studies, as it constitutes a good trade-off between thermal donor formation rate and the maximum concentration obtained.

Alternatively, the effective time $t_{eff}$ can be determined by means of abacuses giving the thermal donor concentration $[TD]_i$ versus the time t of the annealing at 450° C. for different values of the oxygen concentration $[O_i]$.

The effective time $t_{eff}$ can also be calculated considering a different reference temperature from 450° C. Relation (1) and the abacuses will then be adapted in particular on account of the teachings of the article ["Effect of oxygen concentration on the kinetics of thermal donor formation in silicon at temperatures between 350 and 500° C.", Londos C. A. et al., Appl. Phys. Lett. 62 (13), pp. 1525, 1993]. This article also describes the formation kinetics of thermal donors in silicon, but for annealing temperatures comprised between 350° C. and 500° C.

Finally, when several pairs of values $[O_i]$ and $[TD]_i$ are available for the same silicon wafer, a mean annealing time $t_{mean}$ at 450° C. can be calculated. This mean will then constitute a better indicator of the effective time $t_{eff}$.

Step F4 of FIG. 2 consists in determining the original position h of the wafer in its ingot, knowing the effective time $t_{eff}$. For this, the bijection relation between the quantities $t_{eff}$ and h is implemented.

Advantageously, the position h is determined by means of an abacus representative of the function $h(t_{eff})$. Such an abacus enables the position h of the ingot corresponding to a value of the effective time $t_{eff}$ calculated in step F3 to be read easily and quickly. Preferably, this abacus is constructed making the assumption that the function $h(t_{eff})$ is an affine function. The curve of the abacus is therefore a straight line.

To establish the abacus, a plurality of wafers originating from the same ingot are available. The wafers are preferably taken randomly from the batches corresponding to the ingot. Furthermore, as is often the case of substrates intended for the photovoltaic industry, the wafers of the ingot were not subjected to heat treatment with the aim of destroying the thermal donors.

The concentrations $[O_i]$ and $[TD]_i$ are first measured for each wafer, and the different effective time values $t_{eff}$ are then calculated. The steps can be performed as described in the foregoing, with relation with FIG. 1 (steps F1-F3).

Among the set of effective time values $t_{eff}$, it is assumed that the highest value, noted $t_{eff(max)}$, corresponds to the part solidified first, i.e. the top of the ingot (head), and that the lowest value, $t_{eff(min)}$, corresponds to the bottom part (foot), which was solidified last.

On completion of pulling, ingot manufacturers usually discard the bottom and top portions situated at the ends of the ingot, as they contain large quantities of impurities. They are unusable and consequently scrapped. In general these bottom and top portions represent respectively 15% and 5% of the total height of the ingot.

Thus, the highest effective time value $t_{eff(max)}$ corresponds to a position in the ingot of about 5% of the total height, and the lowest effective time value $t_{eff}$ corresponds to a position in the ingot of about 85% (the origin of this relative height corresponding to the head of the ingot).

Starting from this assumption, the line $h(t_{eff})$ can be plotted on the abacus by placing two points, one at 5% and the other at 85% of the total height of the ingot. The abacus thus obtained can be used for all the ingots which was solidified under similar conditions. An abacus is advantageous constructed for each ingot manufacturer and for each pulling method (Czochralski, Bridgman . . . ). For the same pulling technique and the same manufacturer, several abacuses may be necessary if the operating conditions varied sufficiently to modify the cooling profiles of the ingots.

For example purposes, the effective time $t_{eff}$ was measured for 6 Czochralski single-crystal silicon wafers originating from the same ingot. The results are given in table 1 below:

TABLE 1

| Wafer | $t_{eff}$ (min) |
| --- | --- |
| 1 | 168 |
| 2 | 202 |
| 3 | 222 |
| 4 | 62 |
| 5 | 88 |
| 6 | 18 |

The maximum and minimum effective time values $t_{eff}$ are obtained respectively for wafer n° 3 and wafer n° 6. Wafers 3 and 6 therefore correspond to the fractions respectively situated at 5% and 85% of the height of the ingot.

Figure 3:
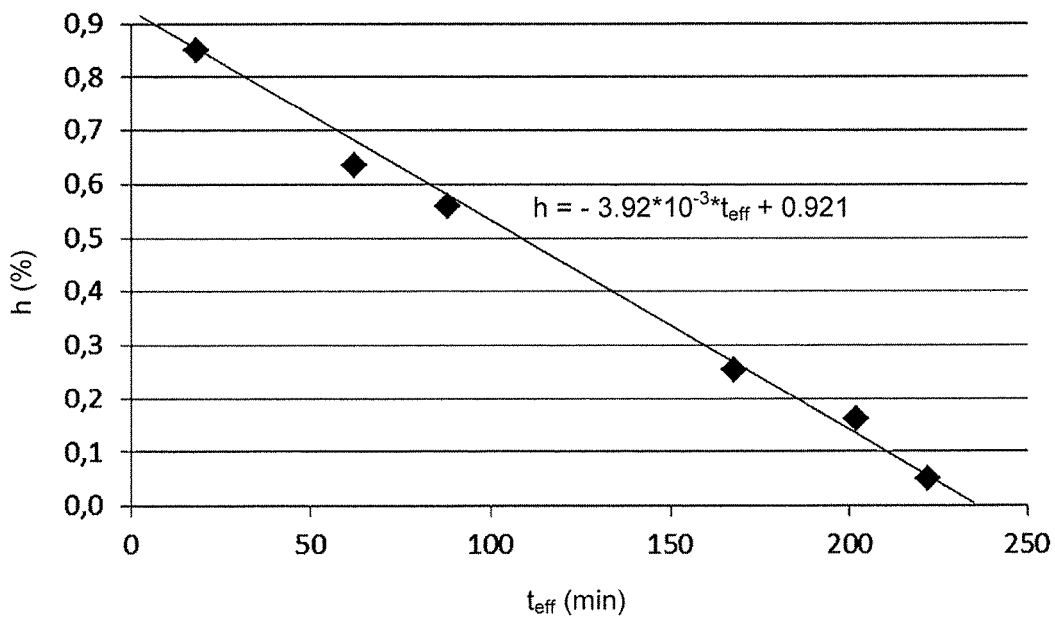
FIG. 3 is an abacus giving the relative position of a wafer in its ingot, versus the equivalent annealing time calculated in step F3 of FIG. 2.

FIG. 3 is a graph of the relative position h in the ingot versus the effective time $t_{eff}$. The two values of $t_{eff}$ obtained previously enable two points to be placed (at the coordinates $\{t_{eff}=18; h=0.85\}$ and $\{t_{eff}=222; h=0.05\}$. A line of equation $h=-3.92*10^{-3}*t_{eff}+0.921$ is able to be drawn using these two extreme points.

This line or its equation will enable the original position h of any subsequent wafer, originating from the same ingot or from an equivalent ingot, to be calculated from the effective time value calculated for this wafer.

With the other values of $t_{eff}$ of table 1, it is possible to verify that the assumption of an affine function is justified. For this, it is however necessary to be in possession of information provided by the ingot manufacturer enabling the heights of wafers 1, 2, 4 and 5 to be determined precisely.

According to the manufacturer data, the position h of wafers 1, 2, 4 and 5 is respectively equal to 0.253, 0.162, 0.636 and 0.560. Transferring these values onto the abacus of FIG. 3, it can be observed that the points coincide with the line of equation $h=-3.92*10^{-3}*t_{eff}+0.921$. Consequently, the assumption according to which $h(t_{eff})$ is an affine function is verified.

This abacus construction method is quick and easy to implement. For more precision, it is preferable to select a large number of wafers in order to come as close as possible to the maximum and minimum values effectively corresponding to the ends of the ingot. In FIG. 1, a factor of about 10 exists between the effective time of the foot of the ingot and that of the head of the ingot. In practice, the number of wafers measured would be considered as being sufficient as and when a ratio $t_{eff(max)}/t_{eff(min)}$ of about 10 is reached.

The FTIR technique, used in steps F1 and F2 for measuring the concentrations $[O_i]$ and $[TD]_i$, requires a wafer with a thickness of more than 300 jam, and optic polished surface state ("mirror" finish) and perfectly parallel surfaces. Consequently, this technique is unsuitable for the photovoltaic industry which uses the substrates originating directly from dicing and with a thickness of less than 200 μm. Furthermore, a FTIR measurement to determine $[TD]_i$ is generally made at very low temperature (4 K) in order to reduce the background noise caused by the absorption of phonons. It is therefore difficult to apply this technique on a large scale.

Thus, to remedy the shortcomings of the FTIR technique, alternative techniques were implemented to determine the concentrations $[O_i]$ and $[TD]_i$. These variants of steps F1 and F2 are described in the following in relation with FIGS. 4 and 5.

Figure 4:
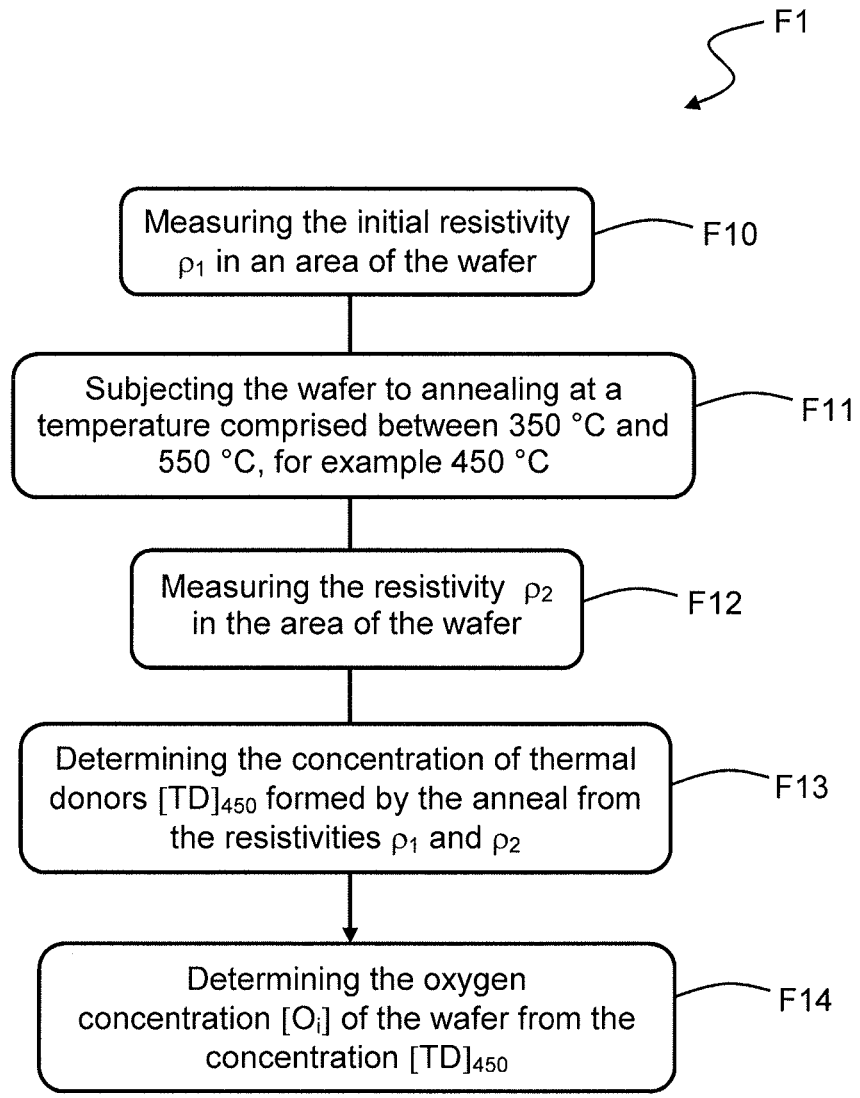
FIG. 4 represents a preferred embodiment of step F1 of FIG. 2.

FIG. 4 therefore represents another technique for determining the interstitial oxygen concentration $[O_i]$. This technique, also based on formation of thermal donors, has been described in detail in French Patent FR2964459, for the oxygen mapping of a silicon wafer.

In FIG. 4, step F1 of determining the concentration $[O_i]$ is broken down into several sub-steps F10 to F14. In F10, the initial electric resistivity $\rho_1$ in an area of the silicon wafer is measured. The resistivity $\rho_1$ takes account of the thermal donors and of the other dopants (for example boron atoms in the case of a p-doped wafer), all originally present in the wafer (in concentration $[TD]_i$ for the thermal donors):

$$\rho_1 = \frac{1}{q \times \mu([B], [TD]_i) \times ([B] - 2[DT]_i)}$$

In the above expression, q is the elementary charge ($q=1.6*10^{-19}$ C) and [B] is the dopant concentration (e.g. boron), μ designates the mobility of the charge carriers which, according to the teachings of Patent FR2964459, depends on the concentration $[TD]_i$, in addition to the dopant concentration [B].

The wafer is then subjected to annealing so as to form additional thermal donors (sub-step F11). The temperature of this annealing is preferably comprised between 350° C.

and 500° C., for example 450° C. The annealing time can vary from about ten minutes to a few hours. The purpose of this annealing is to form new thermal donors, in addition to those formed during solidification of the ingot.

After annealing F11, a new value $\rho_2$ of the electric resistivity is measured, preferably in the same area of the wafer (sub-step F12). The resistivities $\rho_1$ and $\rho_2$ are for example measured by the four-point probes method, the Van der Pauw method or by Foucault current.

The variation of the resistivity $\rho_2$-$\rho_1$ is attributable to the formation of the new thermal donors, when the anneal is performed F11. The resistivity values $\rho_1$ and $\rho_2$ enable the thermal donor concentration $[TD]_{450}$ to be calculated in a sub-step F13.

More particularly, the resistivity $\rho_2$ is written:

$$\rho_2 = \frac{1}{q \times \mu([B], [TD]_i + [TD]_{450}) \times ([B] - 2[TD]_i - 2[TD]_{450})}$$

In this expression, in comparison with that of the resistivity $\rho_1$, the concentration $[TD]_{450}$ of thermal donors formed during the anneal F11 is added to the initial thermal donor concentration $[TD]_i$.

As in Patent FR2964459, the initial concentration $[TD]_i$ can be assumed to be much lower than the concentration $[TD]_{450}$ of thermal donors formed during the anneal F11 ($[TD]_i \ll [TD]_{450}$, and than the dopant contents, in the example of boron as dopant $[TD]_i \ll [B]$). The dopant concentration $[B]$ is then taken from the resistivity value $\rho_1$ measured before the anneal F11, and the concentration $[TD]_{450}$ is calculated from the resistivity value $\rho_2$, knowing the dopant concentration.

The initial quantity $[TD]_i$ of thermal donors that was measured in step F2 can also be taken into account in calculating $[TD]_{450}$. This calculation mode is the most precise and will therefore be preferentially used.

Finally, in F14, the oxygen concentration $[O_i]$ in the silicon wafer is determined from the concentration $[TD]_{450}$ and from the annealing time F11. A mathematical equation, for example relation (1) above, or other abacuses giving the oxygen concentration for different annealing times and temperatures, can be used for this purpose.

During solidification of the ingot, between 500° C. and 350° C., and during annealing F11, the interstitial oxygen concentration hardly varies as the effective time $t_{eff}$ and the annealing time are short. The value measured in F14 therefore truly represents the quantity of oxygen initially present in the portion of the ingot (i.e. before cooling of the latter).

Figure 5:
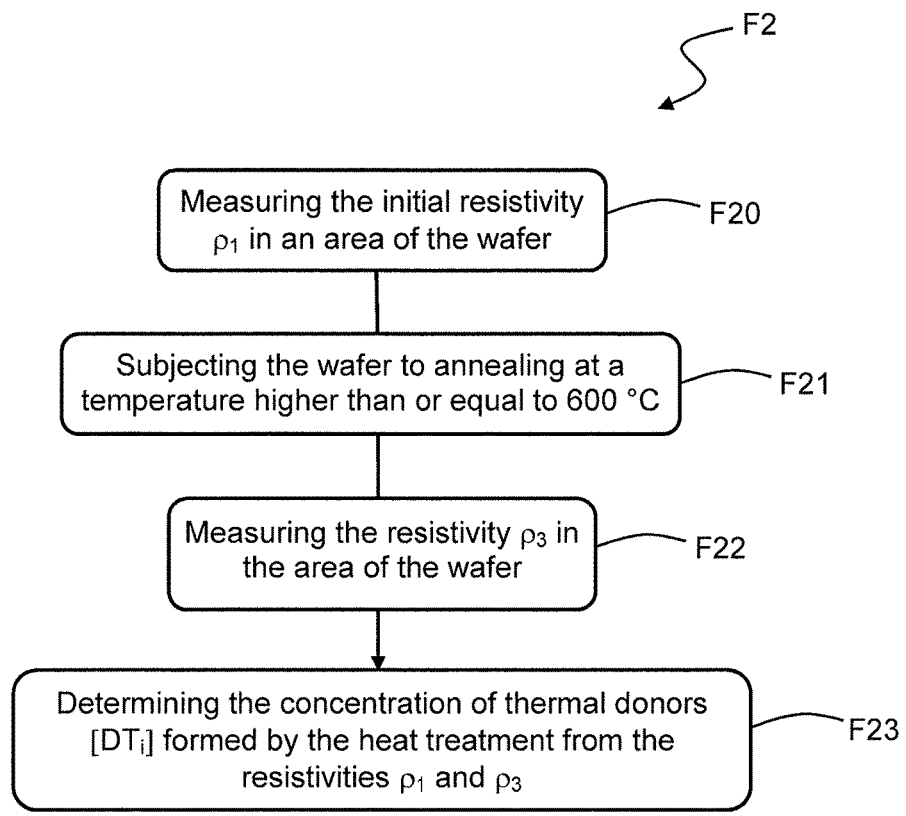
FIG. 5 represents a preferred embodiment of step F2 of FIG. 2.

FIG. 5 represents a variant of implementation of step F2 the purpose of which is to determine the thermal donor concentration $[TD]_i$. This variant again uses the principle of a resistivity variation caused by the thermal donors, as was described in relation with FIG. 4. It therefore comprises resistivity measurement steps F20 and F22, respectively before (resistivity $\rho_1$) and after (resistivity $\rho_3$) an annealing step F21. However, unlike the annealing F11 of FIG. 4, the purpose of the annealing F21 is not to form additional thermal donors, but on the contrary to destroy those initially present in the wafer. The annealing F21 is performed at a temperature higher than or equal to 600° C., for example for 30 minutes.

The value $\rho_3$ measured after the anneal F21 is the resistivity of the wafer devoid of thermal donors. Consequently, it only depends on the dopant concentrations. In the example of boron as the only dopant, its expression is the following:

$$\rho_3 = \frac{1}{q \times \mu([B]) \times [B]}$$

The value $\rho_1$ measured before the anneal F21 represents the state of the wafer as it is delivered by the ingot manufacturer. As indicated previously, it takes account of the dopants and of the thermal donors formed during solidification of the ingot, in concentration $[TD]_i$.

Thus, in a step F23, the dopant contents are calculated from the resistivity $\rho_3$, and the concentration $[TD]_i$ is then calculated from the resistivity $\rho_1$ and from the dopant concentrations.

The measuring techniques of FIGS. 4 and 5 are applicable whatever the thickness of the wafers and the surface state. They only require resistivity measurements and heat treatments, which are steps that are easy to perform and non-destructive. These two techniques are therefore suitable for the semiconductor industry, and are more particularly suitable for solar quality silicon substrates.

Steps F1 and F2 of FIGS. 4 and 5 can be performed independently from one another. They can also be used concomitantly.

When steps F1 and F2 of FIGS. 4 and 5 are sequenced in this order (as suggested by FIG. 2), step F20 of FIG. 5 can be eliminated as a reference value is already available: the value $\rho_1$ measured at the outset, in F10. After the concentration $[O_i]$ has been determined in F14, annealing F21 will then be performed directly followed by measurement of a third resistivity value $\rho_3$ (in F22). Finally, the initial thermal donor concentration $[TD]_i$ will be calculated from the resistivities $\rho_3$ ($[TD]=0$) and $\rho_1$ ($[TD]=[TD]_i$).

Furthermore, when step F2 follows on from step F1, the thermal donor destruction annealing F21 is performed after the thermal donor formation annealing F11. There will therefore no longer be any thermal donors in the wafer on completion of the process. This sequencing of steps is therefore advantageous if it is desired to circumvent the thermal donors, for the subsequent electronic or photovoltaic component fabrication steps.

If on the contrary it is desired to take advantage of the electric properties conferred by the thermal donors, the initial thermal donor concentration $[TD]_i$ of the wafer can be measured (step F2-FIG. 5) before measuring the interstitial oxygen concentration $[O_i]$ (step F1-FIG. 4). In this case, the first step will be to destroy the initial thermal donors before creating new ones. As in the previous case, only three resistivity measurements will have to be made: initial resistivity $\rho_1$ before the anneal F20 ($[TD]=[TD]_i$), resistivity $\rho_3$ after the anneal F20 ($[TD]=0$), and resistivity $\rho_2$ after the anneal F10 ($[TD]=[TD]_{450}$).

In other words, the wafer localisation method is not limited to any order of steps F1 and F2.

As indicated in the above, it is preferable to know the initial thermal donor concentration $[TD]_i$ before measuring the interstitial oxygen concentration $[O_i]$. Measurement of $[O_i]$ is in fact more precise, taking account of the initial thermal donors in calculation of the concentration $[TD]_{450}$ (step F13—from the expression of $\rho_2$). Performing annealing at high temperature F21 after the annealing F11 at 450° C. also enables a better precision to be obtained on the measurement of $[O_i]$. In the reverse order, the anneal F21 can influence the thermal donor formation kinetics when the next anneal is performed F11 and therefore distort measurement of the interstitial oxygen concentration $[O_i]$.

Thus, in a preferred embodiment, the steps of FIGS. 4 and 5 are intertwined so that the anneal F21 follows on from the anneal F11 and that the concentration $[TD]_i$ is determined before the concentration $[O_i]$. The order of the steps is advantageously the following:

F10 (=F20): measurement of resistivity $\rho_1$ ($[TD]=[TD]_i$);
F11: annealing at 350° C.-500° C.;
F12: measurement of resistivity $\rho_2$ ($[TD]=[TD]_i+[TD]_{450}$);
F21: annealing at 600° C. or more;
F22: measurement of resistivity $\rho_3$ ($[TD]=0$);
F23: calculation of $[TD]_i$ from $\rho_1$ and $\rho_3$;
F13: calculation of $[TD]_{450}$ from the $\rho_1$, $\rho_2$ and $[TD]_i$; and
F14: determination of $[O_i]$ from $[TD]_{450}$.

Although the method has been described in relation with a Cz monocrystalline silicon wafer, it could be applied to other forms of silicon (quasi-monocrystalline or polycrystalline structure) and other semiconductor materials. Germanium is for example a potential candidate, as oxygen-base thermal donors are also formed when crystallisation of the latter takes place. Finally, the ingot from which the wafers originate can be crystallised by means of pulling techniques other than the Czochralski or Bridgman processes, provided that the different portions of the ingot are subjected to different cooling kinetics.

The invention claimed is:

1. A method for determining an original position of a wafer in an ingot made from semiconductor material, comprising the following steps:
    measuring an interstitial oxygen concentration in one area of the wafer;
    measuring a concentration of thermal donors formed in said area of the wafer during a previous solidification of the ingot;
    determining an effective time of a thermal donor formation anneal undergone by the wafer when solidification of the ingot took place from the thermal donor concentration and the interstitial oxygen concentration; and
    determining the original position of the wafer in the ingot from the effective time.

2. The method according to claim 1, wherein the thermal donor concentration is determined from first and second resistivity values measured in said area of the wafer respectively before and after heat treatment for the purposes of destroying the thermal donors.

3. The method according to claim 2, wherein the interstitial oxygen concentration is determined from the first resistivity value and a third resistivity value measured in said area of the wafer respectively before and after an additional thermal donor formation anneal.

4. The method according to claim 3, wherein the thermal donor destruction heat treatment is performed after the additional thermal donor formation anneal.

5. The method according to claim 1, wherein the original position of the wafer is determined according to the following steps:
    selecting a plurality of wafers originating from the same ingot;
    determining an effective time value for each wafer;
    placing two points corresponding to the minimum and maximum effective time values from the set of previously determined effective time values on an abacus; and
    plotting a straight line between the two points.

6. The method according to claim 5, wherein the minimum and maximum effective time values are associated with original positions equal to 5% and 85% of the total height of the ingot.

7. The method according to claim 2, wherein the original position of the wafer is determined according to the following steps:
    selecting a plurality of wafers originating from the same ingot;
    determining an effective time value for each wafer;
    placing two points corresponding to the minimum and maximum effective time values from the set of previously determined effective time values on an abacus; and
    plotting a straight line between the two points.

8. The method according to claim 3, wherein the original position of the wafer is determined according to the following steps:
    selecting a plurality of wafers originating from the same ingot;
    determining an effective time value for each wafer;
    placing two points corresponding to the minimum and maximum effective time values from the set of previously determined effective time values on an abacus; and
    plotting a straight line between the two points.

9. The method according to claim 4, wherein the original position of the wafer is determined according to the following steps:
    selecting a plurality of wafers originating from the same ingot;
    determining an effective time value for each wafer;
    placing two points corresponding to the minimum and maximum effective time values from the set of previously determined effective time values on an abacus; and
    plotting a straight line between the two points.

* * * * *